United States Patent
Sepper et al.

(10) Patent No.: US 11,730,745 B1
(45) Date of Patent: Aug. 22, 2023

(54) KIT AND NEW METHOD OF TREATMENT FOR SKIN BASAL CELL AND SQUAMOUS CELL CARCINOMA

(71) Applicants: Alexander Sepper, New York, NY (US); Dennis Tubian, New York, NY (US); John Navi, New York, NY (US)

(72) Inventors: Alexander Sepper, New York, NY (US); Dennis Tubian, New York, NY (US); John Navi, New York, NY (US)

( * ) Notice: Subject to any disclaimer, the term of this patent is extended or adjusted under 35 U.S.C. 154(b) by 12 days.

(21) Appl. No.: 17/970,160

(22) Filed: Oct. 20, 2022

(51) Int. Cl.

| | |
|---|---|
| A61K 31/573 | (2006.01) |
| A61K 9/00 | (2006.01) |
| A61K 31/05 | (2006.01) |
| A61K 31/12 | (2006.01) |
| A61K 31/196 | (2006.01) |
| A61K 31/352 | (2006.01) |
| A61K 31/405 | (2006.01) |
| A61K 31/4172 | (2006.01) |
| A61K 31/727 | (2006.01) |
| A61K 33/04 | (2006.01) |
| A61K 47/02 | (2006.01) |
| A61K 47/10 | (2017.01) |
| A61K 47/12 | (2006.01) |
| A61K 47/14 | (2017.01) |
| A61K 47/18 | (2017.01) |
| A61K 47/20 | (2006.01) |
| A61K 47/22 | (2006.01) |
| A61K 47/34 | (2017.01) |
| A61K 47/36 | (2006.01) |
| A61K 47/44 | (2017.01) |

(Continued)

(52) U.S. Cl.
CPC .......... *A61K 31/573* (2013.01); *A61K 9/0014* (2013.01); *A61K 31/05* (2013.01); *A61K 31/12* (2013.01); *A61K 31/196* (2013.01); *A61K 31/352* (2013.01); *A61K 31/353* (2013.01); *A61K 31/405* (2013.01); *A61K 31/4172* (2013.01); *A61K 31/727* (2013.01); *A61K 33/04* (2013.01); *A61K 47/02* (2013.01); *A61K 47/10* (2013.01); *A61K 47/12* (2013.01); *A61K 47/14* (2013.01); *A61K 47/18* (2013.01); *A61K 47/20* (2013.01); *A61K 47/22* (2013.01); *A61K 47/34* (2013.01); *A61K 47/36* (2013.01); *A61K 47/44* (2013.01); *A61P 35/00* (2018.01)

(58) Field of Classification Search
None
See application file for complete search history.

(56) References Cited

FOREIGN PATENT DOCUMENTS

RU 2451531 C1 5/2012

Primary Examiner — Kyung S Chang

(57) ABSTRACT

A kit, compositions, and methods of treatment for skin basal cell and squamous cell carcinomas The compositions include caustic and base parts. In a broad embodiment, the caustic part includes oxalic acid dihydrate 4-6 wt/vol %, lactic acid 90% 0.5-2 wt/vol %, pyruvic acid 0.20-0.90 wt/vol %, acetic acid 2-6 wt/vol %, nitric acid 65% 30-60 wt/vol %, trichloracetic acid 2-4 wt/vol %, and distilled water to 100%. In the broad embodiment, the base part includes cetyl alcohol 3-5 wt/vol %, glyceryl monostearate (GMS) 2-4 wt/vol %, ritachol-1000 (emulsifier) 10-20 wt/vol %, dimethicone (200/200 fluid) 3-7 wt/vol %, sesame oil 3-7 wt/vol %, hyaluronic acid sodium salt 0.2-0.5 wt/vol %, xanthan gum 0.1-0.3 wt/vol %, polyethylene glycol-400 5-15 wt/vol %, titanium dioxide 0.2-0.6 wt/vol %, preservative complex 4-8 wt/vol %, phenoxyethanol 0.5-3 wt/vol %, sodium sulfite (Na2SO3) 0.5-4, and distilled water to 100%.

3 Claims, 4 Drawing Sheets

(51) Int. Cl.
*A61P 35/00* (2006.01)
*A61K 31/353* (2006.01)

KIT AND NEW METHOD OF TREATMENT FOR SKIN BASAL CELL AND SQUAMOUS CELL CARCINOMA

FIELD OF THE INVENTION

The field of the present invention relates to a topical treatment of carcinoma.

BACKGROUND OF THE INVENTION

Basal cell (BC) and squamous cell (SC) carcinomas are most often treated with surgery to remove all of the cancer and some of the healthy tissue around it. Options include curettage and electrodessication (electro-surgery), Mohs surgery (microscopically controlled surgery), excisional surgery, radiation therapy, photodynamic therapy, cryosurgery, laser surgery, topical medications.

Curettage and electrodessication, also called C & E treatment, involves removing the surface of the skin cancer with a scraping instrument (a curet) and then searing the base of the cancer with an electric needle. This treatment is often used for small or very superficial squamous cell cancers of the skin.

Laser therapy. An intense beam of light vaporizes growths, usually with little damage to surrounding tissue and with a reduced risk of bleeding, swelling and scarring. Laser treatment may be an option for very superficial skin lesions.

Freezing. This treatment involves freezing cancer cells with liquid nitrogen (cryosurgery). It may be an option for treating superficial skin lesions. Freezing might be done after using a scraping instrument (curet) to remove the surface of the skin cancer.

Photodynamic therapy. Photodynamic therapy combines photosensitizing drugs and light to treat superficial skin cancers. During photodynamic therapy, a liquid drug that makes the cancer cells sensitive to light is applied to the skin. Later, a light that destroys the skin cancer cells is shined on the area.

The present invention is a new approach to establish the effective topical treatment of skin cancer with good outcomes and results.

BRIEF DESCRIPTION OF THE INVENTION

The invention comprises compositions and methods for treatment for basal cell and squamous cell carcinomas.

BRIEF DESCRIPTION OF THE DRAWINGS

The drawings are photographs of actual treatment of a 50×50 mm necrotized carcinoma tumor progressing over 30 days using the composition and method of the invention disclosed herein.

DETAILED DESCRIPTION OF THE INVENTION

Figure 1:
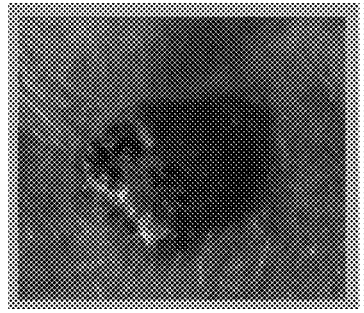
FIG. 1: Carcinoma before treatment
Figure 1:
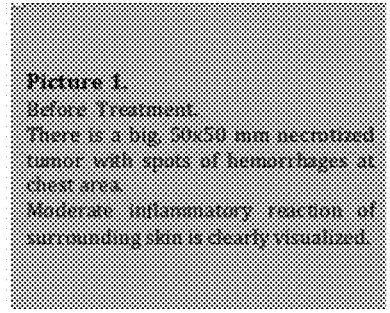
Figure 2:
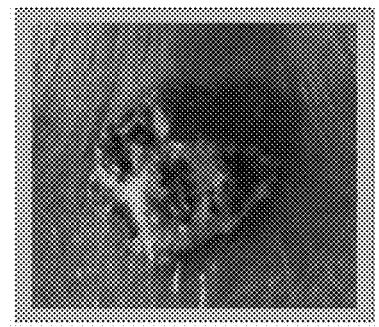
FIG. 2: 3 min. after application of treatment solution
Figure 2:
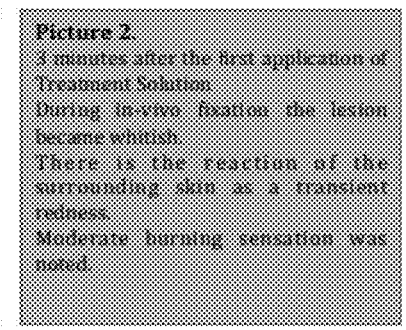
Figure 3:
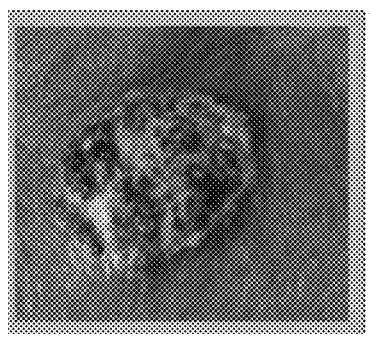
FIG. 3: 10 min. after application of treatment solution
Figure 3:
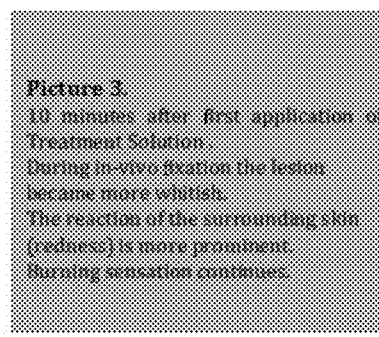
Figure 4:
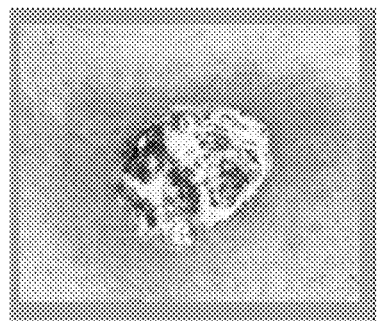
FIG. 4: 20 min. after $2^{nd}$ application of treatment solution
Figure 4:
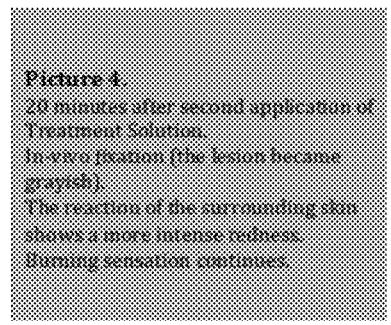
Figure 5:
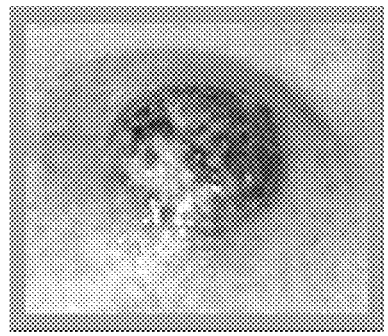
FIG. 5: 45 min. after $2^{nd}$ application of treatment solution
Figure 5:
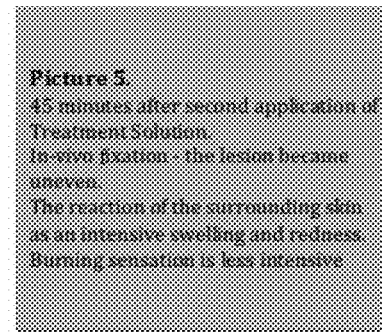
Figure 6:
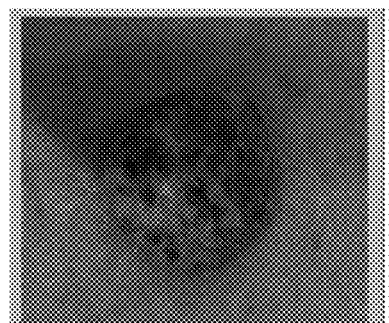
FIG. 6: 6 hrs. after treatment
Figure 6:
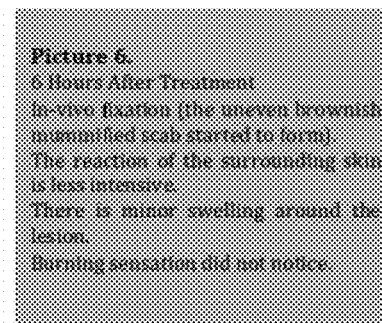
Figure 7:
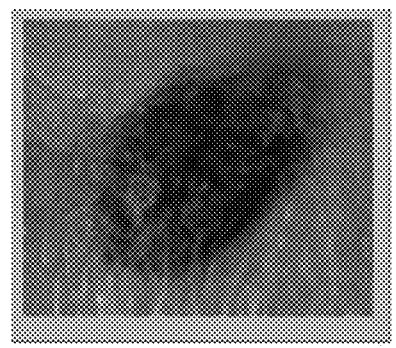
FIG. 7: 3 days after treatment
Figure 7:
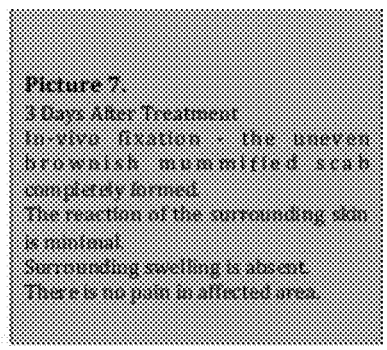
Figure 8:
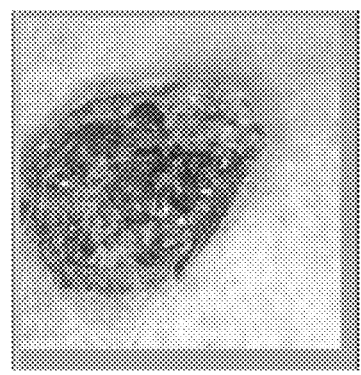
FIG. 8: 10 days after treatment
Figure 8:
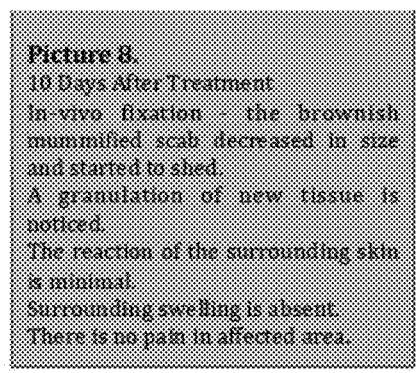
Figure 9:
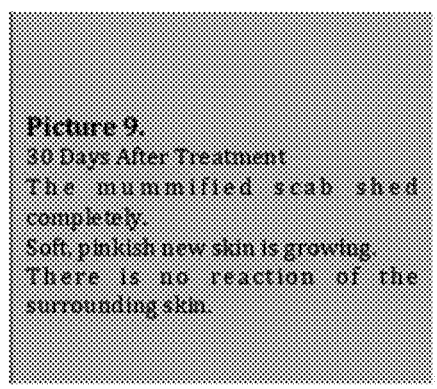
FIG. 9: 30 days after treatment. Health skin regenerated.

The invention comprises a kit and compositions for treatment for basal cell and squamous cell carcinomas. The compositions comprise a number of components, compounded by specific methods and applied using a specific clinical regimen which has been proven to achieve positive clinical outcomes.

General Disclosures

This specification incorporates by reference all documents referred to herein and all documents filed concurrently with this specification or filed previously in connection with this application, including but not limited to such documents which are open to public inspection with this specification. All numerical quantities mentioned herein include quantities that may be plus or minus 5%, or 10% or 15% or 20% of the stated amount in every case, including where percentages are mentioned. As used in this specification, the singular forms "a, an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. For example a composition "comprising" or "which comprises" ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example, "at least 1" means 1 or more than 1, and "at least 80%" means 80% or more than 80%. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). When, in this specification, a range is given as "(a first number) to (a second number)" or "(a first number)-(a second number)", this means a range whose lower limit is the first number and whose upper limit is the second number. For example, "from 40 to 70 microns" or "40-70 microns" means a range whose lower limit is 40 microns, and whose upper limit is 70 microns. The term 'compounding' in this disclosure is related to mixing one or more ingredients to provide a pharmaceutical preparation, i.e. a preparation designed to elicit a physiological effect.

When discussing the amount of a compound in a final LIQUID formulation, we may use the relative units of Percent Volume (v/v). Typically, percent volume written as '% Vol' or 'Volume percent' or 'volume/volume percent' or 'v/v %'. This term is used when preparing solutions of liquids. Volume percent is defined as: v/v %=[(volume of solute)/(volume of solution)]×100%. Note that volume percent is relative to the volume of solution, not the volume of solvent. For example, wine is about 12% v/v ethanol. This means there is 12 ml ethanol for every 100 ml of wine. It is important to realize liquid and gas volumes are not necessarily additive. If you mix 12 ml of ethanol and 100 ml of wine, you will get less than 112 ml of solution. Alternatively, in a liquid formulation, quantities can be given in terms of relative percent concentration by weight of solute in a solution by volume (sometimes given as the relative units wt/vol % or % wt/vol or wt/vol or wt/v or w/v). To determine the weight percent of a solution, divide the mass of solute by mass of the solution (solute and solvent together) and multiply by 100 to obtain percent. The percent by weight formula=gram of solute/100 g of solution. Quantities in a solid formulation are given wt/wt %, also called weight fraction, sometimes shown as wt/wt or % wt/wt or wt/wt %.

Amounts of treatment compositions and penetration enhancer applied during the treatment protocols may vary from the precise amounts mentioned in the examples. Likewise time and duration of application may vary.

When the word "beaker" is used, it is understood that any suitable container may equally be employed.

Compositions of the Invention

The invention utilizes several compositions, as follows.

Treatment Composition #1.

| INGREDIENT | CONCENTRATION (wt/vol %) |
|---|---|
| Treatment Composition #1, part (A) - the so called "caustic part". | |
| In a broad embodiment: | |
| Oxalic acid dihydrate | 4-6 |
| Lactic acid 90% | 0.5-2 |
| Pyruvic acid | 0.20-0.90 |
| Acetic acid | 2-6 |
| Nitric acid 65% | 30-60 |
| Trichloracetic acid | 2-4 |
| Distilled water | to 100% |
| In one exemplary embodiment: | |
| Oxalic acid dihydrate | 5.925 |
| Lactic acid 90% | 1.325 |
| Pyruvic acid | 0.042 |
| Acetic acid | 4.005 |
| Nitric acid 65% | 50.700 |
| Trichloracetic acid | 3.003 |
| Distiled water | to 100% |
| Treatment Composition #1, part (B) - the "base part" | |
| In a broad embodiment: | |
| Cetyl Alcohol | 3-5 |
| GlycerylMonostearate (GMS) | 2-4 |
| Ritachol-1000 (emulsifier) | 10-20 |
| Dimethicone (200/200 Fluid) | 3-7 |
| Sesame Oil | 3-7 |
| Hyaluronic Acid Sodium Salt | 0.2-0.5 |
| Xanthan Gum (Keltrol-CG-T) | 0.1-0.3 |
| PEG400 | 5-15 |
| Titanium Dioxide | 0.2-0.6 |
| Preservative Complex | 4-8 |
| Phenoxyethanol | 0.5-3 |
| Sodium Sulfite (Na2SO3) | 0.5-4 |
| Distilled Water | to 100% |
| In one exemplary embodiment: | |
| Cetyl Alcohol | 4.200 |
| GlycerylMonostearate (GMS) | 3.100 |
| Ritachol-1000 (emulsifier) | 15.000 |
| Dimethicone (200/200 Fluid) | 5.397 |

Treatment Composition #1.

| INGREDIENT | CONCENTRATION (wt/vol %) |
|---|---|
| Sesame Oil | 5.500 |
| Hyaluronic Acid Sodium Salt | 0.343 |
| Xanthan Gum (Keltrol-CG-T) | 0.188 |
| PEG 400 | 11.54 |
| Titanium Dioxide | 0.473 |
| Preservative Complex | 6.150 |
| Phenoxyethanol | 1.363 |
| Sodium Sulfite (Na2SO3) | 1.420 |
| Distilled Water | to 100% |

Treatment Composition #2.

| INGREDIENT | CONC. (wt/vol %) |
|---|---|
| In a broad embodiment: | |
| Dichloropropanoic acid (DPA)oligomer-Selenium complex | 75-95.00 |
| Distilled Water | 3-24.5 |
| Selenium Dioxide (SeO2) | 0.5-3.0 |
| In one exemplary embodiment: | |
| Dichloropropanoic acid (DPA)oligomer-Selenium complex | 90.00 |
| Distilled Water | 9.00 |
| Selenium Dioxide (SeO2) | 1.00 |

Treatment Composition #3.

| INGREDIENT | CONC. (wt/vol %) |
|---|---|
| In a broad embodiment: | |
| Dimethylsylfoxide (DMSO) | 30-50 |
| b-Cyclodexrine (HPBC) | 3-7 |
| Keltrol (Xanthan Gum) | 1-3 |
| Polyethilene Glycol - 400 (PEG-400) | 3-7 |
| Heparin | 0.1-0.5 |
| Hydrocortisone Acetate | 0.2-0.5 |
| Sodium Pyroglutamate | 5-9 |
| Ergosterole | 3-5 |
| Gallic Acid - 3,4,5-Trihydroxybenzoic acid | 1-3 |
| Glycyrrhizic Acid | 1-4 |
| Selinium Dioxide | 0.40-1.0 |
| Histidine | 1-4 |
| Diclofenac (Prostaglandin Synthase Inhibitor) | 2-5 |
| Indomethacin (Prostaglandin Synthase Inhibitor) | 0.3-0.7 |
| Resveratrol (a polyphenol) | 0.1-2 |
| Curcumin | 0.4-0.7 |
| Genistein | 0.4-0.7 |
| EpigalocatechinGalate (Catechin) | 0.4-0.6 |
| Luteolin | 0.4-0.6 |
| Imidazolidinyl Urea | 0.3-0.7 |
| Distilled water | to 100% |
| In one exemplary embodiment: | |
| Dimethylsylfoxide (DMSO) | 45.77 |
| b-Cyclodexrine (HPBC) | 5.00 |
| Keltrol (Xanthan Gum) | 2.00 |
| Polyethilene Glycol - 400 (PEG-400) | 5.00 |
| Heparin | 0.33 |
| Hydrocortisone Acetate | 0.35 |
| Sodium Pyroglutamate | 7.50 |
| Ergosterole | 4.50 |
| Gallic Acid - 3,4,5-Trihydroxybenzoic acid | 1.60 |
| Glycyrrhizic Acid | 2.40 |
| Selinium Dioxide | 0.70 |
| Histidine | 2.50 |
| Diclofenac (Prostaglandin Synthase Inhibitor) | 3.00 |

Treatment Composition #3.

| INGREDIENT | CONC. (wt/vol %) |
| --- | --- |
| Indomethacin (Prostaglandin Synthase Inhibitor) | 0.50 |
| Resveratrol (a polyphenol) | 1.00 |
| Curcumin | 0.60 |
| Genistein | 0.65 |
| EpigalocatechinGalate (Catechin) | 0.55 |
| Luteolin | 0.55 |
| Imidazolidinyl Urea | 0.50 |
| Distilled water | to 100% |

Penetration Enhancer

| INGREDIENT | CONC. (wt/vol %) |
| --- | --- |
| In a broad embodiment: | |
| Dimethylsulphoxide (DMSO) | 25-55 |
| b-Cyclodextrine (HPBC) | 10-25 |
| Laurocapram | 2-6 |
| 2-pyrrolidone | 5-15 |
| Propylene Glycol | 10-30 |
| Terpineol | 5-15 |
| Urea | 5-15 |
| TOTAL | to 100% |
| In one exemplary embodiment: | |
| Dimethylsulphoxide (DMSO) | 36 |
| b-Cyclodextrine (HPBC) | 10 |
| Laurocapram | 4 |
| 2-pyrrolidone | 10 |
| Propylene Glycol | 20 |
| Terpineol | 10 |
| Urea | 10 |
| TOTAL | to 100% |

Treatment Procedure

Treatment requires topical application of the compounds of the invention, applied in a specific routine. Below is a step-by-step procedure for treating a carcinoma using the composition of the invention. Amounts applied may vary.

1. Check the skin cancer lesion. Determine the following parameters:

size of the lesion (cm), depth of the lesion (mm), involvement of surrounding skin tissues including redness, inflammation, flakiness, bleeding, edema.

Disinfect affected area with alcohol and remove any skin flakes with an alcohol wipe.

2. Prepare ex-tempore the Treatment Composition #1. On a glass plate carefully mix a) caustic composition and b) base composition in the proportions 50:50 wt/wt. This is Treatment Composition #1. Use glass or plastic implement for proper mixing to create a homogenous composition.

Figure 10:
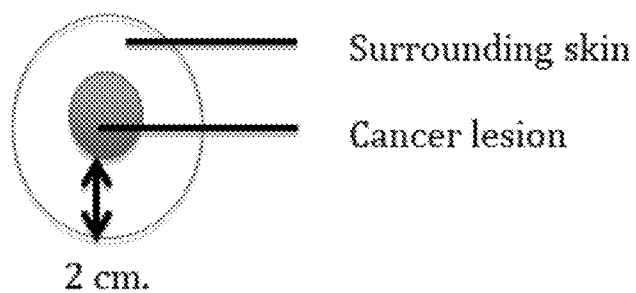
FIG. 10: schematic showing area of application of protective gel.

3. Apply a protective cream (such as a petroleum gel) to the area surrounding the cancer lesion (see FIG. 10). A radius of about 2 mm is usually sufficient.

4. Apply the Treatment Composition #1 to the cancer lesion using glass or plastic implement or a cotton tip swab. The layer c. 1 mm thick should cover the lesion completely.

5. Leave the Treatment Composition #1 on the surface of cancer lesion for: 15-20 minutes on lesions 0.5-0.7 mm in depth; and 25-35 minutes on lesions depth 1.0 and more mm. During this time, monitor the patient's condition. If the patient indicates the strong burning sensation, terminate the application by wiping the treatment composition from the lesion. This step usually is well tolerated. Depending on visual caustic effect on the cancer lesion the treatment composition can be reapplied in 2 hours, or the following day.

6. Necrotic changes of the cancer lesion start to develop in approximately 5-6 hours. The lesion changes color. Initially after the application of Treatment Composition #1 it becomes unevenly whitish-grayish. In 3-4 hours it darkens becoming dark-gray and then brown and black next day. In approximately next 6-8 hours a necrotic scab forms and covers the cancer lesion. The perifocal reaction of redness and tenderness may develop around the treatment site.

7. Within 3 days of the first treatment, apply about 0.5-0.7 g of Penetration Enhancer to facilitate deep penetration of active anticancer ingredients into the depth of lesion.

8. About 40-45 minutes after Penetration Enhancer has been applied, start the applications of Treatment compositions #2 and #3. Apply these one after another with intervals of 2.5-3 hours 2-3 times a day. Apply about 0.25-0.5 g each over a period of 5-6 days.

9. Every day monitor changes in the area of intervention. Check the day when necrotic scab comes off and regeneration tissue of normal skin is formed. A temporary scar can form. In several months, normal cancer-free skin tissue completely replaces the affected area. See the FIGS. 1-9.

Methods of Preparation

Treatment Composition #1:

The below are exemplary embodiments only, and the invention is not limited to the quantities in these formulations.

Cancer-treating effects of treatment composition #1 are based on caustic action of acids of the composition. Treatment composition #1 is made of two parts: part A (caustic) and part B (base) which are mixed together.

A) Caustic Part

| INGREDIENT | CONC. Wt/vol % |
| --- | --- |
| Formulation: | |
| Oxalic acid dihydrate | 5.925 |
| Lactic acid 90% | 1.325 |
| Pyruvic acid | 0.042 |
| Acetic acid | 4.005 |
| Nitric acid 65% | 50.700 |
| Trichloracetic acid | 3.003 |
| Distilled water | 35.00 |
| TOTAL | 100.00 |

Preparation: In a glass beaker add all ingredients, one after another in the sequence shown above, and mix for 40-45 minutes. e.g. with a standard magnetic stirrer, to produce a homogenous mixture. Decant and maintain in a tightly closed air-tight container.

B) Base Part

| INGREDIENT | CONC. Wt/vol % |
| --- | --- |
| Formulation: | |
| Oily (hydrophobic) Phase | |
| Cetyl Alcohol | 4.200 |
| GlycerylMonostearate (GMS) | 3.100 |
| Ritachol-1000 | 15.000 |
| Dimethicone (200/200 Fluid) | 5.397 |
| Sesame Oil | 5.500 |

-continued

B) Base Part

| INGREDIENT | CONC. Wt/vol % |
|---|---|
| [Total Oily (hydrophobic) Phase | 33.197%] |
| Water (hydrophilic) Phase | |
| Distilled Water | 41.070 |
| PEG 400 | 8.225 |
| Hyaluronic Acid (bulking agent) | 0.343 |
| Xanthan Gum (bulking agent) | 0.188 |
| PEG 400 | 3.313 |
| Titanium Dioxide* | 0.473 |
| [Total Water (hydrophilic) Phase | 53.613%] |
| Preservative Complex | 6.150 |
| Distilled water | 58.64% |
| Dehydroacetic acid Sodium Salt | 10.91% |
| Benzethonium chloride | 2.91% |
| Sodium benzoate | 5.34% |
| Potassium sobate | 11.1% |
| Imidazolydinyl urea | 11.1% |
| Total | 100% |

*Titanium dioxide in PEG-400 is prepared in separate beaker and is added to the Oily phase after bulking agents.

Preparation: At Room Temperature, one after another in the sequence shown above, add all components from Oily Phase into heat resistant beaker and heat to about 62° C. to melt all components. Do not exceed 64° C.

At room temperature, slowly add the Hyaluronic Acid and Xanthan Gum ("bulking agents") into the PEG-400 and mix for about 15-20 minutes until full dispersion of Bulking Agents.

We call this mixture "HA-XG".

At room temperature slowly add Titanium Dioxide to PEG-400 and mix for about 15-20 minutes until the Titanium Dioxide is fully dispersed within the mixture.

At room temperature, pour the distilled water into a beaker. And slowly add in the slurry of HA-XG and mix for about 1 hour to form a gel. Heat this mixture, to about 50-60° C., add to it the mixture of Titanium Dioxide and PEG-400.

Before adding the Oily Phase, increase the temperature of the water phase to 75° C.

To the water phase, at about 72-75° C., slowly add oily phase (62-65° C.) and mix thoroughly until a complete emulsion is formed. Once emulsified, quickly reduce temperature of the emulsion to speed-up the process of emulsion crystallization.

At 35° C. add the following to the emulsion: the Preservatives (Hyaluronic Acid and Xanthan Gum) and Sodium Sulfite (Na2SO3). Then mix thoroughly until emulsion cools to room temperature; mix for not less than 90 minutes and not more than 120 minutes.

pH of the Base without adjustment is in a range 7.2-8.2. After completion of preparation the pH of Base is in range 7.2-8.2. We adjust the pH of Base to 6.0.

The Treatment Composition #2 (Selenium): Formulation and Method of preparation

Anti-tumor effects of Selenium are mediated by their ability to inhibit the growth of cancer cells through induction of arrest. Apart from unique anti-cancer efficiency Selenium provides better selectivity between normal and cancer cells. The promising application of Selenium is delivery of active components to certain cells and tissues. There is a reverse correlation between level of Selenium in blood and frequency of development of cancer. Additional treatment with Selenium decreases the frequency of cancer more than 35%.

Formulation and Method of Preparation:
Step 1—Synthesis of DPA (2,2-Dichloropropionic acid) in a Form of Tetraoligomer-Polymer(s):

| INGREDIENT | % |
|---|---|
| Distilled water | 30.00 |
| DPA | 70.00 |
| TOTAL | 100.00 |

Heat the 70% (v/v) solution of DPA (above) to 190° C. under a constant mixing (reflux) for 6 hours. Then cool down to room temperature. Then filter the liquid which is a Dark-Brown liquid.

We call this the "DPA oligomer"

Step 2—Synthesis of a DPA (Dichloropropanoic acid) Oligomer Complexed with Metallic Selenium:

| INGREDIENT | % |
|---|---|
| Metallic Selenium | 0.10 |
| DPA oligomer | 99.90 |
| TOTAL | 100.00 |

Place metallic Selenium in a glass flask and carefully add DPA oligomer and mix (by reflux), heating to 195° C. for 6 hours. Then cool to room temperature and filter the liquid, which is another dark-brown liquid.

We call this the "DPA oligomer-Selenium complex".
Step 3—Synthesis of a DPA Oligomer Complexed with Metallic Selenium and $SeO_2$

| INGREDIENT | % |
|---|---|
| PART 1 | |
| DPA oligomer-Selenium complex | 90.00 |
| PART 2 | |
| Distilled Water | 9.00 |
| Selenium Dioxide (SeO2) | 1.00 |
| TOTAL | 100.00 |

Prepare the 10% solution of Selenium Dioxide above. Then mix the DPA oligomer-Selenium complex with the Selenium Dioxide solution. Mix using a magnetic stirrer for about 12 hours (or overnight). Filter the liquid, which again is a dark brown liquid. This creates what we call a "DPA Oligomer Complexed with Metallic Selenium and SiO2".

The Treatment Composition #3 (Anti-Angiogenic)

Anti-Angiogenic therapy can effectively normalize the tumor vasculature and attenuate vessel growth for a period of time known as the normalization window. The anti-angiogenic treatment may prevent the growth of cancer by blocking new blood vessels from forming. Angiogenesis inhibitor therapy may stabilize the tumor and prevent it from growing further.

Formulation and Method of Preparation:

| PART 1 - Solvent | |
|---|---|
| Dimethylsylfoxide (DMSO) | 45.77 |
| b-Cyclodexrine (HPBC) | 5.00 |

-continued

| PART 2 - Thickeners | |
|---|---|
| Keltrol (Xanthan Gum) | 2.00 |
| Polyethilene Glycol - 400 (PEG-400) | 5.00 |
| Distilled water | 15.00 |
| PART 3 - Antiangiogenic ingredients | |
| Heparin | 0.33 |
| Hydrocortisone Acetate | 0.35 |
| Sodium Pyroglutamate | 7.50 |
| Ergosterole | 4.50 |
| Gallic Acid - 3,4,5-Trihydroxybenzoic acid | 1.60 |
| Glycyrrhizic Acid | 2.40 |
| Selinium Dioxide | 0.70 |
| Histidine | 2.50 |
| Diclofenac (Prostaglandin Synthase Inhibitor) | 3.00 |
| Indomethacin (Prostaglandin Synthase Inhibitor) | 0.50 |
| PART 3 - Flavonoids | |
| Resveratrol | 1.00 |
| Curcumin | 0.60 |
| Genistein | 0.65 |
| EpigalocatechinGalate (Catechin) | 0.55 |
| Luteolin | 0.55 |
| PART 4 - Preservatives | |
| Imidazolidinyl Urea | 0.50 |
| TOTAL | 100.00 |

Part 1—Solvent.

Add HPBC(b-Cyclodextrine) to DMSO. Mix until the solution is clear.

Part 2—Thickeners.

Add Xanthan Gum to PEG-400. Mix until even suspension. Then add the Xanthan Gum in PEG-400 suspension to Distilled water to form a clear gel. Mix for at least 15 minutes.

Product Preparation.

To HPBC (b-Cyclodextrine) in DMSO solvent, step-by-step add all Antiangiogenic ingredients in the order above and then add the Flavonoids and Preservatives.

Mix for at least 60 minutes until all ingredients are solubilized.

Add Thickeners and mix for at least a further 30 minutes.

Agitate for a further 12 hours for complete incorporation of actives into the delivery system.

Product Use

One exemplary treatment employs 0.5 g per application twice a day for 10 days. Check dynamics of any changes in tumor (size, depth) and surrounding skin (inflammation). In case of decrease of tumor size (from 20 to 50%) continue use of the product additional 2 weeks until complete resorption.

The Penetration Enhancer

Formulation:

| INGREDIENT | USAGE % |
|---|---|
| Dimethylsulphoxide (DMSO) | 36 |
| b-Cyclodextrine (HPBC) | 10 |
| Laurocapram | 4 |
| 2-pyrrolidone | 10 |
| Propylene Glycol | 20 |
| Terpineol | 10 |
| Urea | 10 |
| TOTAL | 100 |

Preparation:

Add the appropriate of HPBC to DMSO and mix up to its complete dissolution.

Add one after another all other ingredients until their complete dissolution.

Keep mixing the solution 12 hours (or overnight) for complete incorporation of actives into HPBC system.

Check and adjust pH of the product to 5.8-6.0.

Keep the solution in the UV protected amber bottle.

Illustrated Dynamics of Treatment

See figures which show treatment of a carcinoma over a 30 day period, showing repeated application of treatment solution, degeneration of carcinoma, and eventually healthy skin regeneration.

The invention claimed is:

1. A kit comprising a penetration enhancer and three pharmaceutical treatment compositions for use together in a treatment of a carcinoma, the pharmaceutical treatment compositions comprising a Treatment Composition #1, a Treatment Composition #2, and a Treatment Composition #3;

wherein the treatment composition #1 comprises a mixture of part A and part B, wherein the part A comprises:
a) oxalic acid dihydrate;
b) lactic acid 90%;
c) pyruvic acid;
d) acetic acid;
e) nitric acid 65%;
f) trichloracetic acid; and
g) distilled water;

wherein the part B comprises: a) cetyl alcohol; b) glyceryl monostearate; c) ritachol-1000; d) dimethicone; e) sesame oil; f) hyaluronic acid sodium salt; g) xanthan gum; h) polyethylene glycol (PEG)-400; i) titanium dioxide; j) preservative complex; k) phenoxyethanol; l) sodium sulfite; and m) distilled water;

wherein the treatment composition #2 comprises:
a) dichloropropionicacid (DPA)oligomer-selenium complex;
b) distilled water; and
c) selenium dioxide;

wherein the treatment composition #3 comprises:
a) dimethylsylfoxide (DMSO);
b) hydroxypropyl-β-cyclodextrin (HPBC);
c) xanthan gum;
d) polyethylene glycol-400;
e) heparin;
f) hydrocortisone acetate;
g) sodium pyroglutamate;
h) ergosterol;
i) gallic acid (-3,4,5-trihydroxybenzoic acid);
j) glycyrrhizin acid;
k) selenium dioxide;
l) 1-histidine;
m) diclofenac;
n) indomethacin;
o) resveratrol;
p) curcumin;
q) genistein;
r) epigalocatechingalate;
s) luteolin;
t) imidazolidinyl urea; and
u) distilled water;

wherein the penetration enhancer comprises:
a) dimethylsulphoxide (DMSO);
b) hydroxypropyl-β-cyclodextrin (HPBC);
c) laurocapram;
d) 2-pyrrolidone;
e) propylene glycol;

f) terpineol; and
g) urea;
and wherein the penetration enhancer and the three treatment compositions of the kit are adapted for application, over a period of time, to skin basal cell and squamous cell carcinoma in the following order: the Treatment Composition #1, the penetration enhancer, the Treatment Composition #2, and the Treatment Composition #3.

2. The kit of claim 1, wherein the part A comprises:
a) oxalic acid dihydrate in a concentration of 4-6 wt/vol %;
b) lactic acid 90% in a concentration of 0.5-2 wt/vol %;
c) pyruvic acid in a concentration of 0.20-0.90 wt/vol %;
d) acetic acid in a concentration of 2-6 wt/vol %;
e) nitric acid 65% in a concentration of 30-60 wt/vol %;
f) trichloracetic acid in a concentration of 2-4 wt/vol %; and
g) distilled water in a concentration to 100%;
wherein the part B comprises:
a) cetyl alcohol in a concentration of 3-5 wt/vol %;
b) glyceryl monostearate in a concentration of 2-4 wt/vol %;
c) ritachol-1000 in a concentration of 10-20 wt/vol %;
d) dimethicone in a concentration of 3-7 wt/vol %;
e) sesame oil in a concentration of 3-7 wt/vol %;
f) hyaluronic acid sodium salt in a concentration of 0.2-0.5 wt/vol %;
g) xanthan gum in a concentration of 0.1-0.3 wt/vol %;
h) PEG 400 in a concentration of 5-15 wt/vol %;
i) titanium dioxide in a concentration of 0.2-0.6 wt/vol %;
j) preservative complex in a concentration of 4-8 wt/vol %;
k) phenoxyethanol in a concentration of 0.5-3 wt/vol %;
l) Sodium sulfite in a concentration of 0.5-4 wt/vol %; and
m) distilled water in a concentration to 100% wt/vol %;
wherein the Treatment Composition #2 comprises:
a) dichloropropionic acid (DPA) oligomer-selenium complex in a concentration of 75-95.00 wt/vol %;
b) distilled water in a concentration of 3-24.5 wt/vol %; and
c) selenium dioxide in a concentration of 0.5-3.0 wt/vol %;
wherein the Treatment Composition #3 comprises:
a) dimethylsulphoxide (DMSO) in a concentration of 30-50 wt/vol %;
b) hydroxypropyl-β-cyclodextrin (HPBC) in a concentration of 3-7 wt/vol %;
c) xanthan gumin a concentration of 1-3 wt/vol %;
d) polyethylene glycol-400 in a concentration of 3-7 wt/vol %;
e) heparin in a concentration of 0.1-0.5 wt/vol %;
f) hydrocortisone acetate in a concentration of 0.2-0.5 wt/vol %;
g) sodium pyroglutamate in a concentration of 5-9 wt/vol %;
h) ergosterol in a concentration of 3-5 wt/vol %;
i) gallic acid (-3,4,5-trihydroxybenzoic acid) in a concentration of 1-3 wt/vol %;
j) glycyrrhizin acid in a concentration of 1-4 wt/vol %;
k) selenium dioxide in a concentration of 0.40-1.0 wt/vol %;
l) l-histidine in a concentration of 1-4 wt/vol %;
m) diclofenac in a concentration of 2-5 wt/vol %;
n) indomethacin in a concentration of 0.3-0.7 wt/vol %;
o) resveratrol in a concentration of 0.1-2 wt/vol %;
p) curcumin in a concentration of 0.4-0.7 wt/vol %;
q) genistein in a concentration of 0.4-0.7 wt/vol %;
r) epigalocatechingalate in a concentration of 0.4-0.6 wt/vol %;
s) luteolin in a concentration of 0.4-0.6 wt/vol %;
t) imidazolidinyl urea in a concentration of 0.3-0.7 wt/vol %; and
u) distilled water in a concentration to 100% wt/vol %;
wherein the penetration enhancer comprises:
a) dimethylsulphoxide (DMSO) in a concentration of 25-55 wt/vol %;
b) b-cyclodextrin (HPBC) in a concentration of 10-25 wt/vol %;
c) laurocapram in a concentration of 2-6 wt/vol %;
d) 2-pyrrolidone in a concentration of 5-15 wt/vol %;
e) propylene glycol in a concentration of 10-30 wt/vol %;
f) terpineol in a concentration of 5-15 wt/vol %; and
g) urea in a concentration of 5-15 wt/vol %;
and wherein the penetration enhancer and the three treatment compositions of the kitare adapted for application, over a period of time, to skin basal cell and squamous cell carcinoma in the following order: the Treatment Composition #1, the penetration enhancer, the Treatment Composition #2, and the Treatment Composition #3.

3. The kit of claim 1, wherein the Dichloropropionic acid (DPA) oligomer-selenium complex comprises: 2,2-Dichloropropionic acid complexed with metallic selenium.

* * * * *